US007195878B2

(12) United States Patent
Cleator

(10) Patent No.: US 7,195,878 B2
(45) Date of Patent: Mar. 27, 2007

(54) DEVICE AND METHOD FOR FECAL TESTING

(75) Inventor: Iain G. M. Cleator, Vancouver (CA)

(73) Assignee: Cryo-Genomics, Vancouver (CA)

(*) Notice: Subject to any disclaimer, the term of this patent is extended or adjusted under 35 U.S.C. 154(b) by 350 days.

(21) Appl. No.: 10/953,273

(22) Filed: Sep. 30, 2004

(65) Prior Publication Data

US 2006/0068400 A1 Mar. 30, 2006

(51) Int. Cl.

*C12Q 1/68* (2006.01)
*C12M 1/00* (2006.01)
*C07H 21/02* (2006.01)
*C07H 21/04* (2006.01)

(52) U.S. Cl. ...................... 435/6; 435/283.1; 536/23.1; 536/24.3

(58) Field of Classification Search .................... 435/6, 435/283.1; 536/23.1, 24.3
See application file for complete search history.

(56) References Cited

U.S. PATENT DOCUMENTS

| | | | | |
|---|---|---|---|---|
| 3,996,006 | A | 12/1976 | Pagano | 23/253 |
| 4,225,557 | A | 9/1980 | Hartl et al. | 422/56 |
| 4,259,964 | A | 4/1981 | Levine | 422/61 |
| 4,365,970 | A | 12/1982 | Lawrence et al. | 422/58 |
| 4,367,750 | A | 1/1983 | Levine | 422/61 |
| 4,578,358 | A | 3/1986 | Oksman et al. | 436/66 |
| 4,645,743 | A | 2/1987 | Baker et al. | 436/66 |
| 4,742,002 | A | 5/1988 | Guadagno | 435/28 |
| 4,789,629 | A | 12/1988 | Baker et al. | 435/7 |
| 4,808,379 | A | 2/1989 | Wardlaw et al. | 422/56 |
| 5,100,619 | A | 3/1992 | Baker et al. | |
| 5,106,582 | A | 4/1992 | Baker | |
| 5,171,529 | A | 12/1992 | Schreiber | |
| 5,182,191 | A | 1/1993 | Fan et al. | 422/61 |
| 5,196,167 | A | 3/1993 | Guadagno et al. | 422/56 |
| 5,238,847 | A | 8/1993 | Steinbiss et al. | 422/61 |
| 5,264,181 | A | 11/1993 | Schreiber | |
| 5,310,680 | A | 5/1994 | Baker et al. | |
| 5,391,498 | A | 2/1995 | Baker et al. | |
| 5,747,344 | A | 5/1998 | Cleator | |
| 5,922,544 | A * | 7/1999 | Miyai et al. | 435/6 |
| 5,948,687 | A | 9/1999 | Cleator | |
| 6,303,304 | B1 | 10/2001 | Shuber et al. | |
| 6,413,747 | B1 * | 7/2002 | Kato et al. | 435/91.2 |
| 6,627,414 | B2 | 9/2003 | Billing-Medel et al. | |
| 2003/0138819 | A1 * | 7/2003 | Gong et al. | 435/6 |
| 2003/0138941 | A1 * | 7/2003 | Gong et al. | 435/287.2 |
| 2005/0277204 | A1 * | 12/2005 | Hollis et al. | 436/518 |
| 2006/0029972 | A1 * | 2/2006 | Lorenz | 435/6 |

FOREIGN PATENT DOCUMENTS

| | | |
|---|---|---|
| CA | 2 286 328 | 10/1998 |

OTHER PUBLICATIONS

Mandel, J.S., et al; "Reducing Mortality from Colorectal Cancer by Screening for Fecal Occult Blood"; *The New England Journal of Medicine*; vol. 328, No. 19; May 13, 1993; pp. 1365-1371.
Winawer, S.J.; "Colorectal Cancer Screening Comes of Age"; *The New England Journal of Medicine*; Vool. 328, No. 19; May 13, 1993; pp. 1416-1417.

* cited by examiner

*Primary Examiner*—Ethan Whisenant
(74) *Attorney, Agent, or Firm*—Nixon & Vanderhye

(57) ABSTRACT

A specimen testing device having a first panel with at least two apertures, a second panel with at least two apertures opposite the apertures in said first panel, a sheet disposed between the first and second panels for receiving a specimen through the apertures, the sheet in the apertures in said first panel having first, second and third portions disposed on opposite sides of a longitudinal axis of the apertures. First aperture covers are mounted on the first panel and overlie the apertures in the first panel. Second aperture covers are mounted on the second panel and overlie the apertures in the second panel. The first and second aperture covers in the first and second panels are movable independently of each other to expose the first, second and third portions of the sheet.

24 Claims, 5 Drawing Sheets

DEVICE AND METHOD FOR FECAL TESTING

The present invention relates to a device for testing fecal matter, and to a method of testing using such a device.

BACKGROUND OF THE INVENTION

It is well known that colorectal cancer and large polyps bleed into the stool. Use of guaiacum for the detection of blood was described in "The Scarlet Letter" by Sherlock Holmes as being sensitive but unreliable. The problem has been that guaiacum detects oxidizing agents of which blood is only one, and red meat and other oxidizing agents also can test positive.

A typical form of fecal occult blood testing known as Hemoccult II® utilizes a guaiac-treated test sheet upon which a specimen of fecal material is smeared. A developing solution is applied to the opposite side of the sheet yielding a blue color, which suggests that blood may be present in the fecal specimen. The drawback of this approach is that a high percentage of false positives is obtained from patients who in fact do not have a cancer or polyp. A false positive result in the test often results in expensive testing of patients who in fact have simply consumed a lot of meat just prior to the test.

One approach to overcome the high incidence of false positives has been to make the test paper sensitive enough to detect up to 2% of blood but not sensitive enough to produce too many false positives. A disadvantage of this compromise approach is that because of the reduced sensitivity, a number of cancers and polyps are not detected.

In an effort to increase sensitivity, the Hemoccult® SENSA system was devised (which results in detecting as little as 1000 micrograms of blood per ml of stool). However, this system results in a higher incidence of false positives requiring unnecessary invasive tests.

Alternative approaches to cutting down on false positives have involved placing patients on specific diets designed to restrict intake of animal proteins and other sources of false positives. Despite these efforts, large numbers of false positives still occur. One reason for this is the very long time it can take for food to pass through the bowel in certain patients.

A specific test for human hemoglobin has been devised. This test—the HemeSelect® test (now called Immudia-sp®)—theoretically registers only human hemoglobin and not animal blood from meat or other agents and therefore theoretically does not require the patient to be on a special diet. Another possible advantage is that human blood from the upper gastrointestinal tract may be digested by the time it reaches the stool and the only human blood detected would be that from the distal bowel. A serious drawback of the Immudia-sp® test is that it is expensive for a screening test and requires specially trained individuals to perform and read the test.

Devices and method for screening fecal occult blood specimens are described and claimed in U.S. Pat. Nos. 5,747,344 and 5,948,687. The entire disclosures of those two patents are herein incorporated by reference.

In recent years there have been significant advances in DNA/RNA testing of fecal matter. Present tests are very expensive often costing hundreds of dollars, and involve a whole stool specimen rather than a sample.

A need continues to exist for an inexpensive and easy-to-use fecal test which has a minimal incidence of false positives and can be readily used in a doctor's office. The invention of the present application seeks to meet that need.

SUMMARY OF THE INVENTION

In accordance with one aspect of the present invention, there is provided a testing device including a first panel with three apertures in the first panel; a second panel with three apertures in the second panel opposite the three apertures in the first panel; a sheet disposed between the first and second panels for receiving a specimen through the apertures, the sheet in the apertures in the first panel having first and second and third portions disposed about a transverse axis of the apertures; first aperture covers mounted on the first panel and overlying the apertures in the first panel; second aperture covers mounted on the second panel and overlying the apertures in the second panel, the first and second aperture covers being movable independently of each other to expose the first and second and third portions of the sheet. The first and second and third portions of the sheet are provided with indicating means for locating where specimen is to be placed on the sheet. The indicating means in the second portion is comprised of one or more zones which are removable from said sheet, and may be defined by perforations. The indicating means in the third portion is comprised of a zone which is also removable from the sheet typically by way of perforations and is impregnated with one or more compounds for preventing degradation of DNA/RNA in a sample applied to the third portion.

According to a preferred aspect, the first and second panels are rectangular. In a further preferred aspect, the apertures in the first panel extend at right angles to the apertures in the second panel. The apertures may be rectangular, square, round or oval.

Typically, the aperture covers in the first panel are hingedly mounted along a hinge line extending transversely of the first panel, and the aperture covers in the second panel are hingedly mounted along a hinge line extending longitudinally of the second panel. The first, second and third portions of the sheet may be divided by one or more dividing regions, which may comprise a hydrophobic strip.

In a further aspect, the first and second panels each have three apertures, with the three apertures in the second panel being opposite the three apertures in the first panel. Each of the three apertures in the first and second panels has a respective aperture cover which overlies portions of the sheet in each of the three apertures. The first and second panels typically have printed matter thereon, and an inner surface of the first and second aperture covers is generally provided with a non-stick wax layer. The sheet may if desired be supported on a support panel disposed between the first and second panels.

In a further aspect, there is provided a method of analyzing a specimen using a specimen-testing device as defined above. The method includes, comprises or consists essentially of the steps of obtaining a specimen; opening a first aperture cover on the first panel to expose the first, second and third portions through an aperture; smearing a portion of the specimen on the first, second and third portions through the aperture; closing the first aperture cover to overlie the aperture; opening a second aperture cover on the second panel to expose the first portion of the sheet carrying the specimen; and applying a reagent to the first portion of the sheet. A zone of the second and third portions is typically removed from the sheet for further analysis. The specimen may be a fecal specimen, a urine specimen, a blood specimen, a sputum specimen, a body fluid specimen or a DNA/RNA specimen.

The sheet may be a single piece of paper, typically filter paper, and may be provided with one or more hydrophobic dividing strips separating the first, second and third portions to prevent or minimize possible leakage of developing solution from the one portion to the other portions. Alternatively, the first, second and third portions may be comprised of three separate pieces of filter paper each separated by a hydrophobic barrier. The paper sheet may be impregnated with reagent (e.g. guaiac) over the entire area thereof, or may be impregnated with reagent (guaiac) only on the first portion and plain unimpregnated filter paper for the second portion. The third portion is typically impregnated with a compound selected from pH buffers, antibiotic(s), a disaccharide sugar (such as Trehalose), a drying agent, a diffusion gel, antibodies to blood or DNA/RNA, and mixtures thereof. These compounds serve to stabilize DNA/RNA to reduce degeneration of the DNA/RNA.

The paper is typically high quality cotton to facilitate preservation of DNA/RNA for analysis of the sample. The hydrophobic material may be wax or other suitable solid organic or inorganic material.

In another preferred aspect, the first and second portions are provided with indicating means for locating where specimen is to be placed on the sheet through the apertures in the first panel, and where developing solution is to be placed through the apertures in the second panel. The indicating means may comprise printed circles or other shapes on the sheet as a visible indicator to the user of where to place the specimen. At least one of the indicating means, usually that in the second and third portions, is preferably comprised of a perforated zone which is removable from the sheet.

In accordance with a further aspect of the invention, the first panel has three apertures extending transversely of the first panel and the second panel has three apertures opposite the three apertures in the first panel, which extend longitudinally of the second panel. In this embodiment, a support panel for the sheet may be provided between the first and second panels with apertures corresponding to the apertures in the first panel. Each of the three apertures in the first panel has a respective cover hingedly mounted along a hinge line extending longitudinally of the longitudinal axis of the panel and overlying a respective aperture and respective first and second portions of the sheet. Each of the three apertures in the second panel has a respective cover which is hingedly mounted on the second panel along a hinge line extending longitudinally of the second panel and overlies the apertures.

According to another preferred feature, the device may carry printed matter on the first panel such as patient details and instructions for opening of the respective covers to reveal the apertures on which the specimen is smeared. Printed matter may also be provided on the second panel, such as instructions to the doctor for conducting testing of specimens.

A further preferred feature of the device is that sticking of the cover to the specimen is prevented by providing the inside surfaces of the respective aperture covers with a non-stick coating. A typical example is a wax layer.

The present invention enjoys numerous advantages. In particular, the device is embodied in one card which readily facilitates transference between the doctor and the patient and between the doctor and another testing location, such as a laboratory. The device is easy to use by the patient and is inexpensive to produce. A particularly important advantage is that the device allows a first test to be carried out by the doctor and, in the event that a specimen is positive, or DNA/RNA testing is indicated for other reasons such as family history or inflammatory bowel disease, subsequent testing can be carried out on the same specimen.

The methodology involves amplifying the DNA/RNA and testing for abnormalities after separating from bacterial and human DNA/RNA. In essence genomics, proteomics and laser flight technology are used to look for changes compared to normal for tumor producing genes, tumor suppressor genes, whether they are expressed, biological markers, and a few genes and messengers which allow delay in the division of the nucleus to permit the gene material to be corrected or the cell to be destroyed (apoptosis) such as p23. Genomics permits testing using a micro-array chip and amplification fluorescent system for up to 20,000 amino acid sequences. Proteomics uses a gel diffusion technique and an applied electric current to delineate different molecular weight and charged proteins and further investigate those, which are not present in the same amount as the normal control. Chip and laser flight technology measures the characteristics of weight and charge using a flight technology. Biological markers can be detected by immunoassay using antibodies.

The third aperture consists of a high quality cotton paper with certain additives present. In order to preserve the stool specimen, the pH should be maintained at around neutral, for example 6.5–7.5, typically about 7.0. This is accomplished by using pH buffered paper which has been impregnated with, for example, 50 ml 0.1 molar potassium dihydrogen phosphate and 29.1 ml of 0.1 molar NaOH. In order to prevent bacterial destruction of the DNA/RNA, use of a solution of an antibiotic such as Flagyl in a dilution $1:10^{-4}$ is used to impregnate the paper. Cotton paper can be impregnated with magnesium carbonate as a drying agent. In order to preserve the DNA/RNA, Trehalose, a disaccharide sugar, in a dilution $1:10^{-4}$ can be used to prevent the destruction of the DNA/RNA which occurs rapidly in untreated stool. The compounds allow for the protection and preservation of DNA/RNA for periods typically up to 11 years. The nature of the compounds varies, depending on whether the specimen is stool or other biological fluid. For stool, the compound would for example include pH buffers, antibiotic(s), a disaccharide sugar such as Trehalose, a diffusion gel, antibodies to blood or DNA/RNA and a drying agent. The paper typically would be high quality cotton to facilitate DNA/RNA testing of the sample. The additives will vary depending on the source of the specimen, but for stool would include pH and osmolarity buffers, antibiotic(s) and a disaccharide sugar such as Trehalose.

If it were indicated to proceed with a DNA/RNA test, the rectangular perforated area would be removed and an eluate obtained using distilled water and buffers which would be used to look for DNA/RNA abnormalities. Examples of these abnormalities are mutant K-ras, p53 tumor suppressor gene, BAT-26 micro satellite instability marker, long DNA/RNA, APC (*Adenomatous polyposis coli*). The sensitivity of the current commercial version using whole stool is approximately 65% for Colo-rectal Cancer (CRC), 30–40% for advanced adenomas, and there is a specificity of 95%. The use of the third aperture adds to conditions detected by a two aperture system (two-tier test), since two entirely different methods of detecting cancer and polyps are involved. Thus, the two tier test identifies about 3% of the screened group of patients who have bleeding in the stool, and this will detect about 90% of cancers and 70% of adenomas. The third aperture will typically detect about 65% of the colo-rectal cancers and 40% of polyps through the shedding of cancer cells and there will be an overlap in patients because the third aperture will detect some cancers and adenomas that are not bleeding at the time of testing. The high specificity of the second test will not add greatly to the 3% who require colonoscopy. The net result is a test with high sensitivity and specificity which avoids unnecessary expensive and invasive tests as are carried out at present.

DETAILED DESCRIPTION OF THE INVENTION

Figure 1:
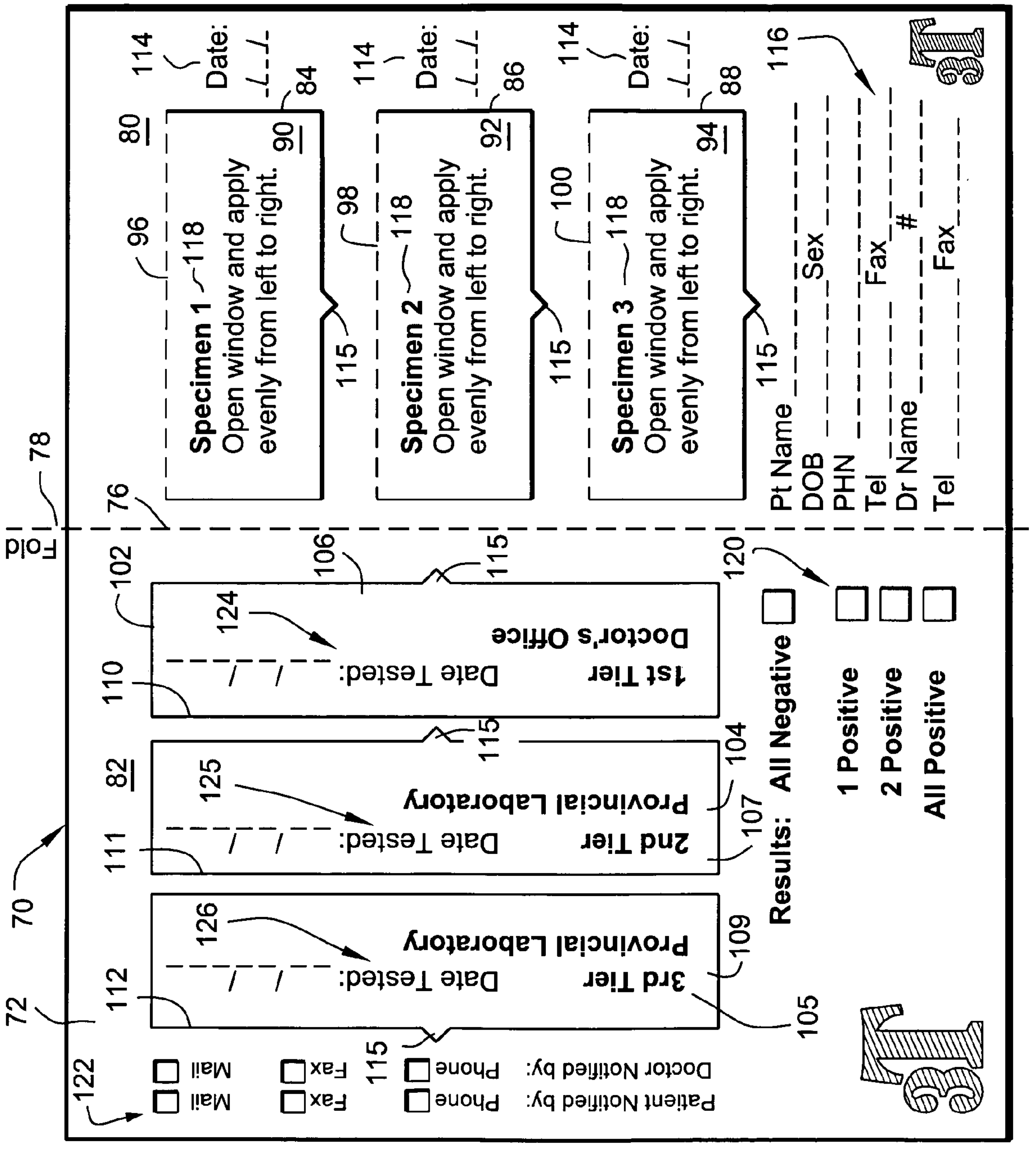
FIG. 1 is a plan view of a device of the invention showing the outside configuration of the foldable sheet.
Figure 2:
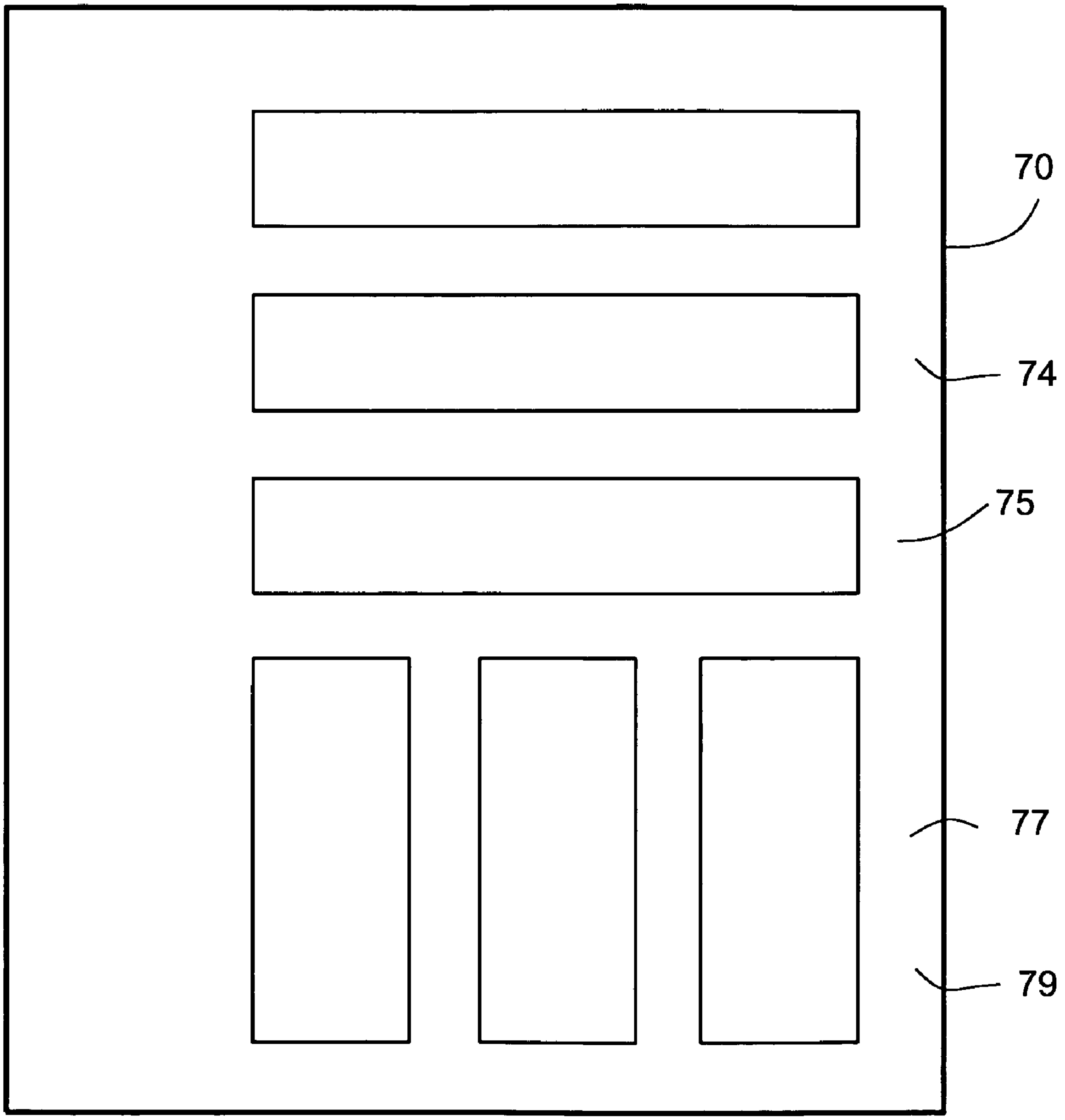
FIG. 2 is a plan view of the inside configuration of the foldable panel of FIG. 1.

Referring to FIGS. 1 and 2, there is shown a foldable panel 70 of the invention. The panel is typically made of paper or cardboard, but may also be fabricated of plastic. The panel has a first outer side 72 and an opposite inner side 74. The panel 70 has a fold line 76 extending along a longitudinal axis 78 forming a first portion 80 on one side of the fold line and a second portion 82 of the other side of the fold line. The first portion 80 is provided with three rectangular apertures 84, 86, 88 extending transversely with respect to the longitudinal axis 78. Each aperture has a respective cover 90, 92, 94 hingedly mounted to the first portion 80 along a respective hinge line 96, 98, 100 extending transversely of the axis 78. Each cover 90, 92, 94 is hingedly movable independently of the others between closed and open positions.

The second portion 82 includes three rectangular apertures 102, 104, 105 extending longitudinally of the axis 78 and opposite the transversely extending apertures 84, 86, 88. Aperture 102 is provided with a cover 106, aperture 104 provided with a cover 107 and aperture 105 is provided with a cover 109. Covers 106, 107 and 109 are each hingedly mounted along a respective hinge line 110, 111, 112, each of which extends longitudinally of the axis 78. Each cover 106, 107, 109 is movable independently of the other between a closed portion and an open position.

The first portion 80 is provided with locations 114 for completion of date(s) on which samples are collected from the patient and patient identifying information 116. In addition, each cover 90, 92, 94 is provided with specimen identification information 118 together optionally with instructions for application of a specimen sample after the cover is opened.

The second portion 82 is provided with locations 120 for reporting results of testing, together with boxes 122 for completion of action taken with respect to the patient and/or doctor. The covers 106, 107, 109 are provided with respective information 124, 125, 126 regarding person or entity conducting analysis of the specimen. Tabs 115 are formed on each cover to assist the user in opening the cover.

FIG. 2 shows the inner sides 74, 79 of the panel 70. The surfaces 75, 77 are typically coated with a hydrophobic material, preferably a waterproof glue such as wax containing an adhesive. The purpose of this hydrophobic material is to prevent contamination or mixing of individual specimens applied through an aperture into the region of an adjacent aperture. In this way, the risk of a specimen spreading and contacting other specimen(s) is minimized. The hydrophobic material also aids in minimizing sticking of the covers to the specimen.

Figure 3:
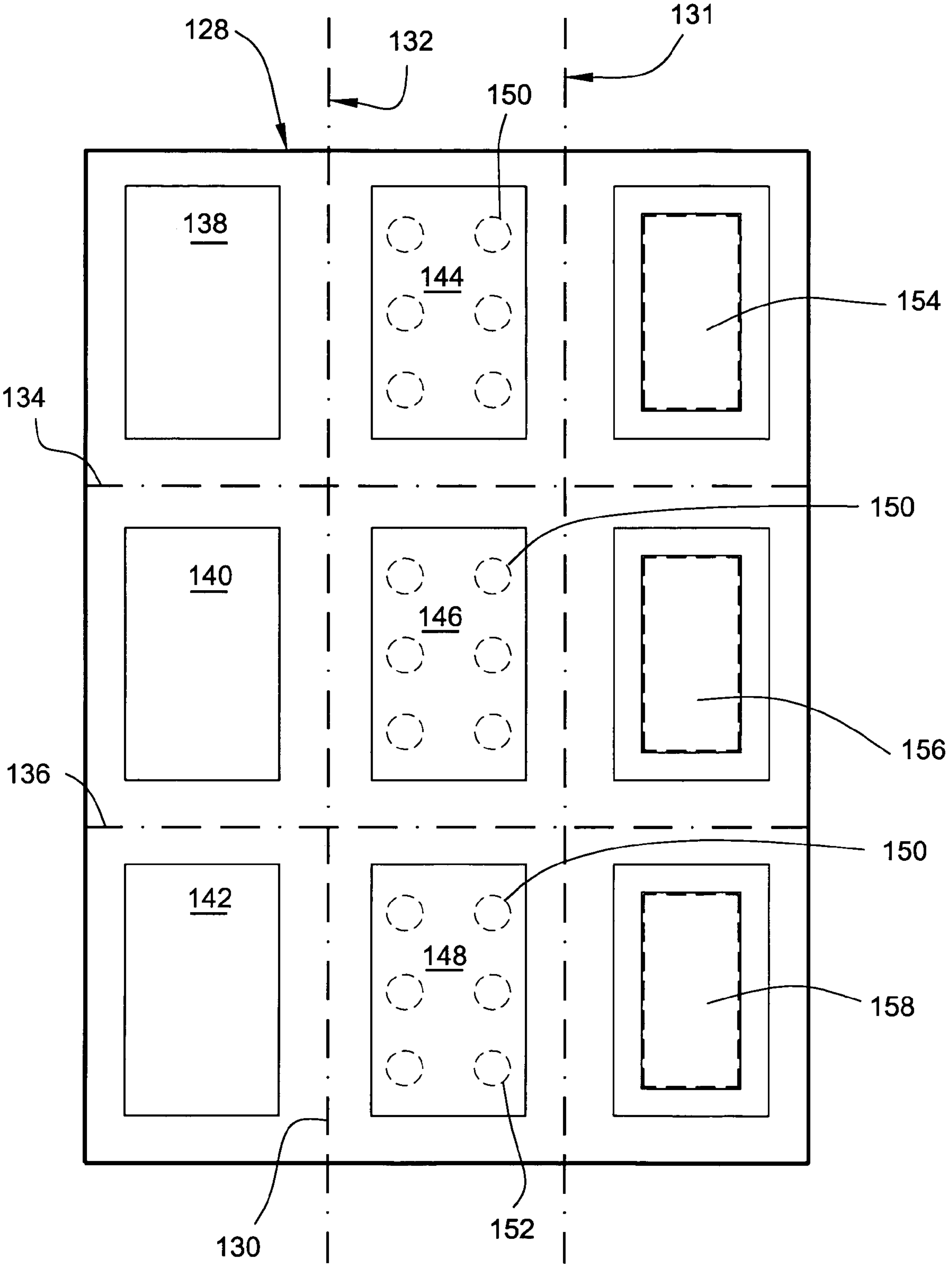
FIG. 3 is a plan view of a simple receiving sheet which is positionable inside the foldable panel of FIG. 1 when the latter is folded.

FIG. 3 shows a sample receiving sheet 128 sized to be received between portions 80, 82 when folded over each other. Sheet 128 is typically made of an absorbent material, usually filter or high grade cotton paper, which is impregnated with a reagent which will react with hemoglobin components from blood and a peroxide solution to form a colored compound. Examples of suitable reagents are guaiac, tetramethyl benzidene, orthotoluidine and other similar chromogens. In the embodiment illustrated herein, the reagent impregnated in the sheet is guaiac. For DNA/RNA testing, the compounds will vary depending on the source of the specimen, but for stool would include pH and osmolarity buffers, antibiotic(s), a diffusion gel, antibodies to blood or DNA/RNA and a disaccharide sugar, such as Trehalose.

To prevent seepage of reagent from one area to another, sheet 128 is provided with strips of hydrophobic material 130, 131 such as wax extending longitudinally parallel to axis 132 and two strips of hydrophobic material 134, 136 such as wax extending transversely of axis 132 and crossing strips 130, 131. The intersecting pattern of strips 130, 131, 134, 136 defines nine regions 138, 140, 142, 144, 146, 148, 154, 156, 158. Regions 144, 146, 148 are each provided with indicating means 150, typically circular zones shown in dashed outline, to assist the user in browsing where to smear the sample on the sheet. The zones may be provided with perforations 152 to enable the zones to be removed from the sheet 128 for subsequent analysis. The sheet 128 may, if desired, be supported on a support member (not shown).

The sheet 128 may be formed from one piece of absorbent paper with hydrophobic strips defining the regions 138, 140, 142, 144, 146, 148, 154, 156, 158. Alternatively, the sheet 128 may be constructed from different absorbent papers, each optionally containing different reagents, with the hydrophobic strips bonding the different papers together to form the sheet. In a further modification, the regions 138, 140, 142, 144, 146, 148, 154, 156, 158 may be comprised of different paper(s) of varying textures, and carrying different colors of reagent. Each region is then bonded together with hydrophobic material to form the completed sheet 128.

DNA/RNA stool specimens undergo considerable amounts of degradation/digestion. There has been some study of this aspect by the Department of Criminal Justice. Dr. Liane R. Martin, STR-Typing of Nuclear DNA/RNA for Human Fecal Matter Using the Qiagen QIAAMP® Stool Mini Kit, describes the difference between the theoretical yield of DNA/RNA ($3.0\times10^5$–$6.0\times10^6$].pg/ml stool. After a week, swabbing or excision both yielded DNA/RNA under the conditions of water immersion (2 hours), air dried for a week, frozen for a week and processed without thawing. All alleles matched that of the subject's reference sample. This means that the stool collected in the way described in this test will be sufficient for testing. Additionally, work has been reported on preservation of stools in rare animals which provides the data for the additives suggested (Society for Conservation Biology, $16^{th}$ Annual Meeting, Jul. 14–19, 2002).

The term "texture" as used herein in connection with the sheet 128 means that the fibrous structure of the sheet material, e.g. paper, may be varied depending on the desired degree of adherence of the sample. The paper should be sufficiently absorbent so that specimen does not easily separate from the sheet after application thereto, for example as the specimen dries out. Generally, the sheet (paper) is chosen such that the fibrous structure of the paper permits at least some of the sample to permeate through the paper and be visible on the other side to that on which the specimen is applied. Generally, the sheet material should be such that at least about 20% by weight, for example about 25 to about 50% by weight, of the specimen permeates through the sheet and is visible on the other side.

Figure 4:
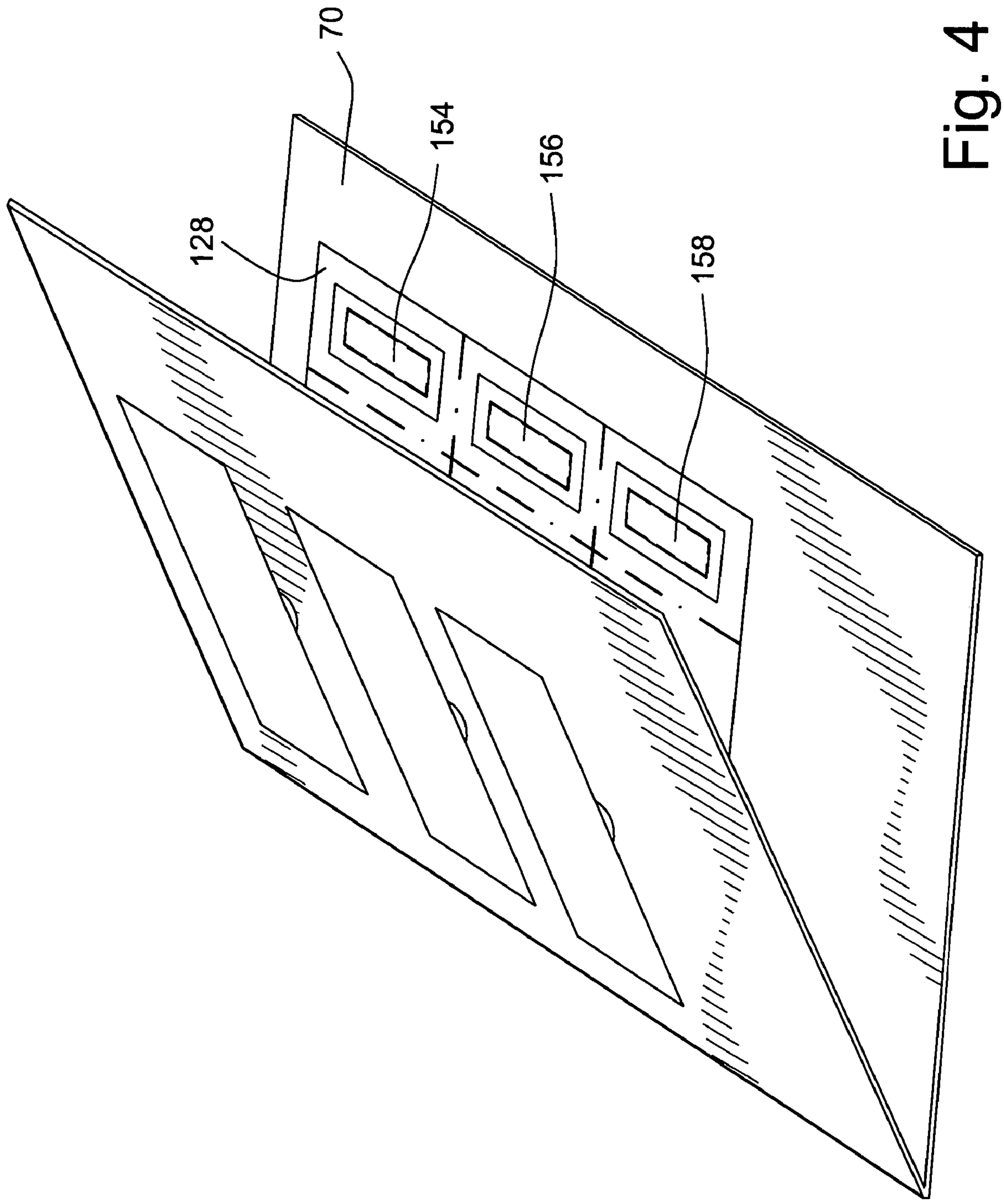
FIG. 4 is a perspective view of the embodiment in partially open configuration comprised of a foldable panel of FIGS. 1 and 2 and a sample receiving sheet of FIG. 3 therebetween.

FIG. 4 is a device of the invention constructed using a foldable panel 70 and a sheet 128. The device is constructed by placing a sheet 128 on an inside surface 74 with the regions 138, 140, 142, 144, 146, 148, 154, 156, 158 aligned with apertures 84, 86, 88. The panel 70 is then folded along fold line 76 to bring the inner surface 74, 79 into face-to-face contact with each other, sandwiching the sheet 128 therebetween with regions in registration with apertures 84, 86, 88 and apertures 102, 104, 105. Adhesive present on surface 74 or surface 79 or both permits the surfaces to be adhered to each other to maintain the resulting device in the folded closed state.

Figure 5:
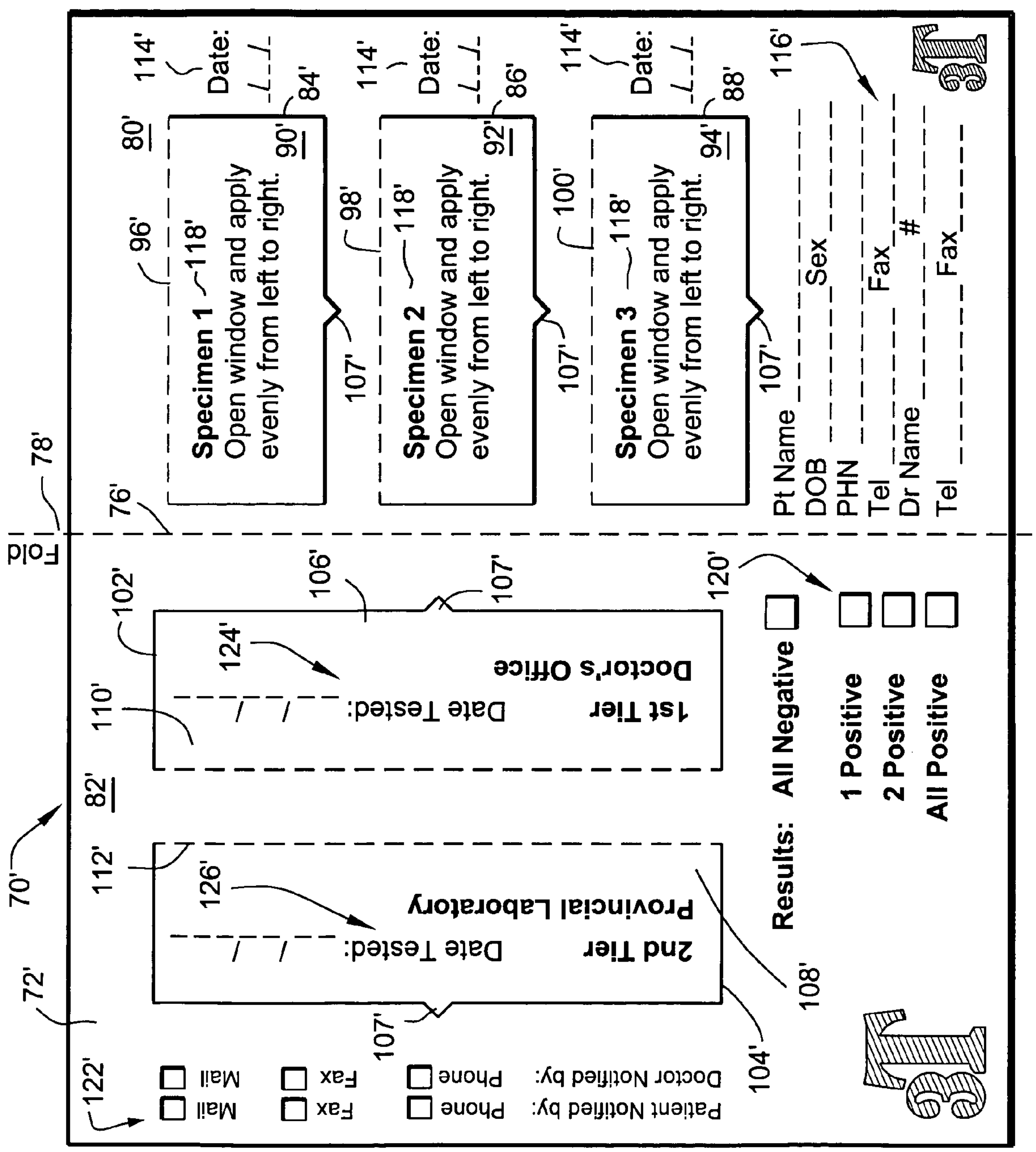
FIG. 5 is a plan view of a further embodiment showing the outside configuration of the foldable sheet.

FIG. 5 shows an embodiment similar to that shown in FIG. 1 except that the second panel 82' includes two rectangular apertures 102', 104' extending longitudinally of the axis 78' and opposite the transversely extending apertures 84', 86', 88'. Aperture 102' is provided with a cover 106', aperture 104' is provided with a cover 108'. Covers 106' and 108' are each hingedly mounted along a respective hinge line 110', 112', each of which extends longitudinally of the axis 78'. Each cover 106', 108' is movable independently of the other between a closed portion and an open portion.

The first portion 80' is provided with locations 114' for completion of date(s) on which samples are collected from the patient and patient identifying information 116'. In addition, each cover 90', 92', 94' is provided with specimen identification information 118' together optionally with instructions for application of a specimen sample after the cover is opened.

The second portion 82' is provided with locations 120' for reporting results of testing, together with boxes 122' for completion of action taken with respect to the patient and/or doctor. The covers 106' 108' are provided with respective information 124', 126' regarding person or entity conducting analysis of the specimen. Tabs 107' are formed on each cover to assist the user in opening the cover.

The invention has been described with reference to analysis of fecal samples for stool occult blood. However, the device may be used for screening and testing of other biological specimens, for example blood and AIDS tests, urine tests, pregnancy tests and DNA/RNA tests. Other biological fluids can be usefully transported and conveniently stored on the DNA/RNA or third aperture which in this aspect could be a single window, or using that only or using the other apertures for a preliminary sensitive but not specific test (inexpensive) to be followed, if positive, by the third aperture. Examples of this would be blood tests (genes for familial breast cancer, leukemia, other cancers, HIV, diabetes, morbid obesity, pregnancy, Hepatitis A,B,C) urine (pregnancy test, complications of pregnancy. Another aspect would be inexpensive storage of biological material—centrifuged specimen of cells from urine, washings, ascitic fluid for later testing or us as a database (with patient's informed consent). Another aspect would be storage of blood and other samples for DNA/RNA testing for specific disorders (heart disease, atherosclerosis, diabetes, morbid obesity.

In use, where a fecal sample is to be analyzed, a cover 90 on the first panel 80 of the device is opened and a fecal specimen is smeared through the aperture on the first, second and third portions 138, 144 and 154 of the exposed sheet 128. The cover is then closed. A second fecal sample taken at a different time as a result of a different bowel movement is then smeared onto the first, second and third portions 140, 146, 156 of the sheet through the second aperture 86 on the first panel, and the cover 92 is closed. The third specimen from yet a different bowel movement at a different time is smeared onto the first, second and third portions 142, 148, 158 through the third aperture 88 on the first panel and the cover 94 is closed.

To conduct a first analysis, the cover 106 on the second panel 82 covering the first portions on which specimen has been applied is opened and developer solution is applied to the circular zone 150 of each first portion. If a specimen tests positive, as evidenced, for example, by the development of a blue color, the cover 104 on the second panel covering the second portions is opened together with the cover on the first panel, and the respective exposed perforated circular zone 150 of the second portion of the sheet carrying the positive specimen is removed with both covers open, e.g. by being punched out of the sheet, and subjected to further analysis (e.g. an immunochemical test).

For DNA/RNA testing, the device is used as follows. Upon indication to proceed with DNA/RNA testing, the cover 105 is opened and the rectangular perforated area 154 is removed and an eluate obtained using distilled water and buffers, which is analyzed for DNA/RNA abnormalities. Examples of such abnormalities are mutant K-ras, p53 tumor suppressor gene, BAT-26 micro satellite instability marker, long DNA/RNA, APC. Colo-rectal cancer has many DNA/RNA mutations associated with it and one test alone is not sufficient. The stool therefore has to be examined for the presence of DNA/RNA with the mutations known to occur with colo-rectal cancer. Similar analyses may be performed on the areas 156 and 158.

Modifications of the invention will be readily apparent to those skilled in the art. For example, embodiments comprising fewer than three apertures in the first and second panels, or embodiments containing more than three apertures in one or both panels, also fall within the scope of the present invention.

In the above description, the apertures are illustrated as rectangular. However, any desired shape may be used, for example oval or circular.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A specimen testing device, comprising:

a first panel;

at least two apertures in said first panel;

a second panel;

at least two apertures in said second panel opposite said at least two apertures in said first panel;

a sheet disposed between said first and second panels for receiving a specimen through said apertures, said sheet in said apertures in said first panel having first, second and third portions disposed about a longitudinal axis of said apertures;

first aperture covers mounted on said first panel and overlying said apertures in said first panel;

second aperture covers mounted on said second panel and overlying said apertures in said second panel;

said first and second aperture covers in said first and second panels being movable independently of each other to expose said first, second and third portions of said sheet;

said third portion of said sheet comprising one or more compounds impregnated therein for preventing degradation of DNA/RNA in a sample applied to said third portion.

2. A device according to claim 1, wherein said first and second panels are rectangular.

3. A device according to claim 1, wherein said apertures in said first and second panels extend longitudinally along said first and second panels.

4. A device according to claim 1, wherein said apertures are rectangular.

5. A device according to claim 1 wherein said apertures are square, round or oval.

6. A device according to claim 1, wherein said aperture covers in said first panel are hingedly mounted along a hinge line extending transversely of said first panel.

7. A device according to claim 1, wherein said aperture covers in the second panel are hingedly mounted along a hinge line extending longitudinally of said second panel.

8. A device according to claim 1, wherein said first and second portions of said sheet are divided by a dividing region.

9. A device according to claim 8, wherein said dividing region comprises a hydrophobic strip.

10. A device according to claim 1, wherein said second and third portions of said sheet are divided by a dividing region.

11. A device according to claim 10, wherein said dividing region comprises a hydrophobic strip.

12. A device according to claim 1, wherein said first and second portions of said sheet are provided with indicating means for locating where specimen is to be placed on the sheet.

13. A device according to claim 12, wherein at least one of said indicating means is comprised of a zone which is removable from said sheet.

14. A device according to claim 13, wherein said zone is defined by perforations.

15. A device according to claim 1, wherein said first and second panels each have three apertures, said apertures in said second panel being opposite said apertures in said first panel.

16. A device according to claim 15, wherein each of said three apertures in said first and second panels has a respective aperture cover which overlies said portions of said sheet in each of said three apertures.

17. A device according to claim 1, wherein said first and second panels have printed matter thereon.

18. A device according to claim 1, wherein an inner surface of said first and second covers is provided with a non-stick wax layer.

19. A device according to claim 1 wherein said sheet is supported on a support panel disposed between said first and second panels.

20. A method of analyzing a specimen using a specimen testing device including a first panel, at least two apertures in said first panel, a second panel, at least two apertures in said second panel opposite said at least two apertures in said first panel, a sheet disposed between said first and second panels for receiving a specimen through said apertures, said sheet in said apertures in said first panel having first, second and third portions disposed about a longitudinal axis of said apertures, first aperture covers mounted on said first panel and overlying said apertures in said first panel, second aperture covers mounted on said second panel and overlying said apertures in said second panel, said first and second aperture covers in said first and second panels being movable independently of each other to expose said first, second and third portions of said sheet, said third portion of said sheet comprising one or more compounds impregnated therein for preventing degradation of DNA/RNA in a sample applied to said third portion, said method comprising the steps of:

(a) obtaining a specimen;

(b) opening a first aperture cover on said first panel to expose said first, second and third portions through an aperture;

(c) smearing a portion of said specimen on said first, second and third portions through said aperture;

(d) closing said first aperture cover to overlie said aperture;

(e) opening a second aperture cover on said second panel to expose said first portion of said sheet carrying said specimen;

(f) applying a reagent to said first portion of said sheet; and (g) testing for DNA/RNA using said third portion.

21. A method according to claim 20, wherein said third portion is removed from said sheet and analyzed for DNA/RNA abnormalities.

22. A method according to claim 21, wherein said abnormalities are mutant K-ras, p53 tumor suppressor gene, BAT-26 micro satellite instability marker, long DNA/RNA, APC.

23. A method according to claim 20, wherein a zone of said second portion is removed from said sheet for further analysis.

24. A method according to claim 20, wherein the specimen is a fecal specimen, a urine specimen, a sputum specimen, a body fluid specimen or a blood specimen.

* * * * *